US005653961A

United States Patent [19]

McNally et al.

[11] Patent Number: 5,653,961
[45] Date of Patent: Aug. 5, 1997

[54] BUTIXOCORT AEROSOL FORMULATIONS IN HYDROFLUOROCARBON PROPELLANT

[75] Inventors: Rebecca A. McNally, St. Paul, Minn.; Gary H. Ward, San Diego, Calif.

[73] Assignee: Minnesota Mining and Manufacturing Company, St. Paul, Minn.

[21] Appl. No.: 414,370

[22] Filed: Mar. 31, 1995

[51] Int. Cl.$^{6}$ .................... A61K 9/12

[52] U.S. Cl. .................... 424/45; 424/46; 514/958

[58] Field of Search .................... 424/45, 47, 46; 514/958

[56] References Cited

U.S. PATENT DOCUMENTS

| | | | |
|---|---|---|---|
| 4,933,331 | 6/1990 | Aubard et al. | 514/179 |
| 5,126,123 | 6/1992 | Johnson | 424/45 |
| 5,190,029 | 3/1993 | Byron et al. | 424/45 |
| 5,225,183 | 7/1993 | Purewal et al. | 424/45 |

FOREIGN PATENT DOCUMENTS

| | | |
|---|---|---|
| 0553298 | 11/1994 | European Pat. Off. . |
| 00062 | 1/1992 | WIPO . |
| 93/04671 | 3/1993 | WIPO . |
| 94/13262 | 6/1994 | WIPO . |
| 94/13263 | 6/1994 | WIPO . |

OTHER PUBLICATIONS

Morén, F. et al. (1993). Aerosols in Medicine. Elsevier Science Publishers, pp. 303–319.

*Primary Examiner*—Raj Bawa
*Attorney, Agent, or Firm*—Gary L. Griswold; Walter N. Kirn; Ted K. Ringsred

[57] ABSTRACT

Pharmaceutical solution aerosol formulations of butixocort propionate as the sole active drug agent and a propellant selected from the group consisting of 1,1,1,2-tetrafluoroethane, 1,1,1,2,3,3,3-heptafluoropropane, and a mixture thereof.

16 Claims, No Drawings

BUTIXOCORT AEROSOL FORMULATIONS IN HYDROFLUOROCARBON PROPELLANT

BACKGROUND OF THE INVENTION

1. Field of the Invention

This invention relates to pharmaceutical aerosol formulations. In another aspect this invention relates to pharmaceutical solution aerosol formulations wherein the propellant comprises a hydrofluoroalkane propellant such as 1,1,1,2-tetrafluoroethane or 1,1,1,2,3,3,3-heptafluoropropane. In another aspect this invention relates to pharmaceutical aerosol formulations containing butixocort propionate.

2. Description of the Related Art

Butixocort propionate (11-beta-hydroxypregn-4-ene-3, 20-dione-21-thiopropionate-17-butyrate is an antiinflammatory steroid disclosed in U.S. Pat. No. 4,933,331 (Aubard et at.).

Current propellant-based pharmaceutical aerosol formulations use a mixture of liquid chlorofluorocarbons as the propellant. Fluorotrichloromethane, dichlorodifluoromethane and dichlorotetrafluoroethane are the most commonly used propellants in aerosol formulations for administration by inhalation. Such chlorofluorocarbons (CFCs), however, have been implicated in the destruction of the ozone layer and their production is being phased out. Hydrofluorocarbon 134a HFC 134a, 1,1,1,2-tetrafluoroethane) and hydrofluorocarbon 227 (HFC 227, 1,1,1,2,3,3,3-heptafluoropropane) are said to be less harmful to the ozone than many chlorofluorocarbon propellants.

Pharmaceutical aerosol formulations for inhalation most commonly contain a drug in the form of solid particles of respirable size suspended in the propellant system. Formulations involving dissolved drug are also known but have generally been less preferred because of the tendency of compounds (including drug substances) to be much more chemically reactive (and therefore unstable) in solution than in the solid state.

SUMMARY OF THE INVENTION

Butixocort propionate has been found to have appreciable solubility in HFA 134a and HFA 227 (at 20° C., HFA 134a dissolves about 0.02% by weight of butixocort propionate and HFA 227 dissolves about 0.03% by weight of butixocort propionate). This level of solubility can lead to particle size increase of the drug in a suspension formulation. It is well known that particles having a diameter of greater than about 10 mm are not suitable for inhalation to the lung. Therefore particle size increase can threaten the utility of a pharmaceutical aerosol formulation for inhalation.

The present invention provides a solution aerosol formulation comprising a propellant system comprising a hydrofluoroalkane selected from the group consisting of 1,1,1,2-tetrafluoroethane, 1,1,1,2,3,3,3-heptafluoropropane, and a mixture thereof, and a therapeutically effective mount of butixocort propionate, wherein the butixocort propionate is dissolved in the formulation.

The present invention also provides a method of treating bronchial asthma, comprising administering via inhalation an amount of a formulation as described above effective to control inflammation associated with bronchial asthma.

The solution formulation of the invention exhibits suitable stability yet eliminates problems associated with increasing particle size. This invention also eliminates other problems encountered with suspension aerosols such as rapid flocculation, irreversible particle aggregation and bulk separation of the drug from the propellant (creaming or settling), all of which affect dose uniformity.

DETAILED DESCRIPTION OF THE INVENTION

All weight percentages recited herein are based on the total weight of the formulation unless otherwise indicated.

The drug butixocort propionate is known and disclosed, e.g., in U.S. Pat. No. 4,933,331 (Aubard et al., incorporated herein by reference). Butixocort propionate is generally present in a formulation of the invention in a therapeutically effective mount, i.e., an mount such that one or more metered volumes of the formulation (e.g., metered volumes of about 50 μL) when delivered to the lung by oral or nasal inhalation contains an mount of medicament effective to exert the intended therapeutic action (e.g., controlling inflammation associated with bronchial asthma). The mount that constitutes a therapeutically effective mount will depend on the particular formulation, the indication being treated and the intended therapeutic effect, and the actuator being used to dispense the formulation. Generally and preferably butixocort propionate constitutes about 0.1 to about 0.9 percent by weight, more preferably about 0.4 to about 0.6 percent by weight of the total weight of the formulation.

The formulation of the invention is a solution formulation, i.e., the butixocort propionate is dissolved in the formulation and the formulation is substantially free of particulate (undissolved) butixocort propionate. Certain steroids are known to exist in several crystalline forms (polymorphs). A formulation of the invention, however, contains butixocort propionate but not a particular crystalline form or polymorph thereof, as the crystalline identity of the drug is lost upon dissolution. Therefore this invention avoids complications that can occur in certain suspension steroid formulations due to in situ changes in crystal form (e.g., crystal polymorphism). Any appropriately soluble form of butixocort propionate can be used in preparing a formulation of the invention.

As noted above, butixocort propionate has been found to have appreciable solubility in HFA-134a and in HFA-227. In most cases, however, the solubility of butixocort propionate in these propellants will not be sufficient to afford a formulation containing a therapeutically effective amount of dissolved butixocort propionate. Therefore it is often necessary or desirable to use a solubilizer in order to further solubilize butixocort propionate (i.e., in order to provide a system in which butixocort propionate is more soluble than in the hydrofluoroalkane propellant alone). Butixocort propionate can be further solubilized in any suitable manner. Well known methods of solubilizing include use of cosolvents for the drug (e.g., alcohols such as ethanol or propylene glycol, dimethyl ether) to aid in drug dissolution, and micellar solubilization of the drug using a surfactant, e.g., a glycerol phosphatide such as lecithin or other such materials enumerated for such purpose in PCT Publication No. WO93/04671 (Oliver et al.). It is sometimes necessary to use a cosolvent for the surfactant in order to dissolve sufficient surfactant to accomplish micellar solubilization of a drug.

The preferred solubilizer for use in a formulation of the invention is ethanol. Ethanol, however, has been found to decrease the respirable fraction of drug if it is used in an excessive mount. A formulation of the invention preferably contains ethanol in an amount effective to further solubilize butixocort propionate in the formulation but less than that amount which causes a decrease in respirable fraction.

Preferably the ethanol constitutes about 3 to about 30 percent by weight of the total weight of the formulation. More preferably, ethanol constitutes about 8 to about 16 percent by weight of the aerosol formulation.

A formulation of the invention contains a propellant system that functions to propel the other components of the formulation through the valve of a metered dose inhaler canister in a manner such that the drug is presented for inhalation by a patient. The propellant system comprises a hydrofluoroalkane propellant. Preferred propellants include 1,1,1,2-tetrafluoroethane, 1,1,1,2,3,3,3-heptafluoropropane, and mixtures thereof in any proportion. The propellant is present in an amount sufficient to propel a plurality of doses from an aerosol canister such as a metered dose inhaler. The propellant preferably constitutes from about 60 to about 98 percent by weight, and more preferably from about 75 to about 90 percent by weight of the total weight of the aerosol formulation. The formulations of the invention are preferably free of chlorofluorocarbons such as fluorotrichloromethane, dichlorodifluoromethane, and dichlorotetrafluoroethane. Most preferably, the hydrofluorocarbon propellant is the only propellant present in the formulations of the invention.

A formulation of the invention can contain suitable excipients (e.g., those disclosed in U.S. Pat. No. 5,225,183, Purewal et at., incorporated herein by reference) in mounts readily determined by those skilled in the art. Certain excipients, e.g., certain surfactants (for optimizing valve function), flavoring agents, and/or water, are beneficial to some embodiments of the invention. For example, it has been found that in some instances the chemical stability of certain formulations of the invention (that is, stability of the formulation to degradation of butixocort propionate) is enhanced by the presence of water. When water is included in a formulation of the invention it will generally be present in an mount of about 0.005 percent to about 1 percent by weight of the total weight of the formulation. Strong inorganic acids (e.g., hydrochloric, nitric, phosphoric, or sulfuric acid) or organic acids (e.g., ascorbic acid, citric acid) can also be incorporated into a formulation of the invention in the manner described in WO94/13262 and WO94/13263 (Jager et al., incorporated herein by reference).

Formulations of the invention optionally further comprise a flavoring agent, e.g., a menthol, in an amount effective to mask the taste of butixocort propionate when an aerosolized dose of the formulation is inhaled orally, e.g., about 0.3 percent by weight of the total weight of the formulation.

Despite the fact that the drug is dissolved, preferred formulations of the invention are stable for a prolonged period of time to degradation of the drug. Preferably a formulation of the invention when stored ten months in an aluminum aerosol vial as described below (Examples 11–50) exhibits a percent drug recovery of at least about 93 percent, more preferably at least about 95 percent.

Formulations of the invention can be prepared by either pressure filling or cold filling techniques, both of which are well known to those skilled in the art. Ethanol and the excipient or excipients, if any, are combined with the propellant. This solution is pressure filled or cold filled into aerosol vials containing the butixocort propionate. Alternatively, the butixocort propionate and any non-volatile excipients are dissolved in ethanol in an aerosol vial. The aerosol vial is then fitted with a valve and pressure filled with the propellant.

Aerosol canisters equipped with conventional valves, preferably metered dose valves, can be used to deliver formulations of the invention. A suitable valve rubber is a nitrile rubber "DB-218") available from American Gasket and Rubber, Schiller Park, Ill.

Conventional aerosol canisters can be used to contain a formulation of the invention. It has been found, however, that certain containers enhance the chemical stability of certain formulations of the invention and/or minimize the absorption of butixocort propionate onto the container walls; accordingly, it is preferred to contain a formulation of the invention within an aluminum aerosol vial.

A formulation of the invention can be administered to the lung by oral or nasal inhalation. Oral inhalation is preferred, and conventional actuators for oral inhalation can be used in connection with a formulation of the invention. Particle size or droplet size of the inhaled dose is important to an inhalable dose form intended to be administered to the lung. Particle size or droplet size and respirable fraction of a propellant based solution aerosol formulation can be affected by the size of the orifice through which the formulation passes. It is preferred to administer a formulation of the invention through an actuator having an orifice diameter of about 0.25 mm (0.010 inch) or less. An example of such an actuator is actuator model M3756, 3M Company.

The examples set forth below are intended to illustrate the invention.

Respirable Fraction

In this assay the respirable fraction (the percent by weight of particles having an aerodynamic particle size of less than 4.7 mm) of the aerosol formulation is determined using an Anderson Cascade Impactor (available from Anderson Sampler Inc., Atlanta, Ga).

The aerosol vial containing the formulation to be tested is primed 5 times. The valve and valve stem are then cleaned with ethanol and dried with compressed air or nitrogen. The aerosol vial and a clean, dry actuator (unless otherwise indicated Model M3756 having an orifice diameter of about 0.25 mm (0.010 inch), 3M) are coupled to the glass throat attached to the top of the impactor using an appropriate firing adaptor. The calibrated vacuum pump (28.3 L/min) attached to the impactor is turned on. The vial is actuated. After the aerosol cloud has disappeared (about 4 seconds), the vial and actuator are disconnected, shaken for about 10 seconds, then reconnected to the throat and actuated again. This procedure is repeated until the vial has been actuated a total of 10 times. The cascade impactor is disassembled and each component is rinsed with diluent. Each solution is analyzed for butixocort propionate content using high performance liquid chromatography or ultraviolet spectroscopy (238 nm). The respirable fraction is calculated as follows:

$$\% \text{ Respirable} = \frac{\text{Butixocort propionate recovered from plates 3-7}}{\text{Butixocort propionate recovered from the throat, 0 jet stage and plates 0-7}} \times 100$$

Percent Degradation Impurities and Percent Drug Recovery

In these assays the percent of degradation impurities and the percent of drug recovered is determined using high performance liquid chromatography.

Sample Solution Preparation

The aerosol vial containing the formulation to be assayed is chilled in dry ice for 20 minutes. The cap is removed and the contents of the vial are poured into a pre-chilled volumetric flask. The propellant is allowed to evaporate. The cap and vial are rinsed with acetonitrile into the volumetric flask. The flask is brought to volume with the indicated diluent. An aliquot of this solution is pipetted into a volumetric flask and the flask is brought to volume with the indicated diluent.

Standard Solution Preparation

A precisely weighed quantity of butixocort propionate is placed into a volumetric flask then dissolved in ethanol or acetonitrile. The flask is brought to volume with the indicated diluent. An aliquot of this solution is pipetted into a volumetric flask and the flask is brought to volume with the indicated diluent.

Procedure

A portion of the standard solution is injected into the HPLC using the parameters indicated below in connection with the either Percent Degradation Impurities or Percent Drug Recovery, as appropriate, and the recorder sensitivity is adjusted to produce peaks at 70–90% of full scale. The chromatogram is obtained and the peak areas are measured. This chromatogram provides a correlation between peak area and weight of butixocort propionate. It also provides the peak areas of impurities present in the raw drug (butixocort propionate) prior to formulating.

A portion of the sample solution is injected into the HPLC under the same conditions as the standard. The chromatogram is obtained and the peak areas are measured.

Percent Degradation Impurities

The percent impurities in the raw drug is determined using the peak areas from the HPLC chromatogram (diluent: acetonitrile; column: 15 cm×4.6 mm Supelco 5 micrometer Supersil LC-18; mobile phase: 30:35:35 methanol:acetonitrile:water containing 0.1 mg perchloric acid per 100 mL of solution; flow rate 1 mL/min; detection: 240 nm UV) of the standard solution and the equation below.

$$\% \text{ impurities in raw drug} = \frac{\text{Sum of the areas of the impurity peaks}}{\text{Sum of the areas of the impurity peaks and the butixocort propionate peak}} \times 100$$

The percent impurities in the sample is obtained by performing the same calculation on the peak areas from the sample chromatogram.

The percent degradation impurities is then determined using the equation below.

$$\% \text{ degradation impurities} = \% \text{ impurities in the sample} - \% \text{ impurities in raw drug}$$

Percent Drug Recovery

This is based on the amount of butixocort propionate in the sample vial before and after storage.

The amount of butixocort propionate that was in the aerosol vial after storage is determined by HPLC (diluent: a solution of 55 volume percent acetonitrile and 45 volume percent water containing 0.05 mg ascorbic acid per 100 mL of solution; column: 15 cm×4.6 mm Supelco 5 micrometer Supersil LC-18; mobile phase: 55:45 acetonitrile/water v/v; flow rate 1:5 mL/min; detection: 240 nm UV) using the area of the butixocort propionate peak from the sample chromatogram and the correlation between peak area and weight of butixocort propionate that is obtained from the standard chromatogram.

The amount of butixocort propionate that was in the aerosol vial when it was first prepared is known.

The percent drug recovery is then determined using the equation given below.

$$\% \text{ drug recovery} = \frac{\text{amount of butixocort propionate after storage}}{\text{initial amount of butixocort propionate}} \times 100$$

Solubility Studies

Solubility of butixocort propionate in P134a, P227, and blends thereof with ethanol, was determined as follows: Drug and the selected propellant system were combined and agitated for a period of seven days at a selected temperature to afford a saturated solution. The solid was filtered off and the supernatant was weighed. The propellant was removed by evaporation and the drug was reconstituted quantitatively. The concentration of the drug in the reconstituted solution was determined and from this the mount and concentration of drug dissolved in the propellant system was calculated. TABLES 1 and 2 show the average of three independent determinations.

TABLE 1

Butixocort Solubility (mg drug/mL propellant)

| Temperature (°C.) | Propellant | |
|---|---|---|
| | 134a | 227 |
| 4 | 0.103 | 0.261 |
| 20 | 0.203 | 0.285 |
| 30 | 0.3 | 0.306 |
| 40 | 0.319 | 0.317 |

TABLE 2

Butixocort Solubility (mg drug/mL propellant), 20°C.

| Weight % Ethanol | Propellant | |
|---|---|---|
| | 134a | 227 |
| 0 | 0.30 | 0.395 |
| 1 | 0.751 | 0.971 |
| 2.5 | 1.757 | 1.113 |
| 5 | 4.177 | 3.853 |
| 7.5 | 6.958 | 6.199 |
| 10 | 9.633 | 8.519 |

EXAMPLE 1

Butixocort propionate (50 mg) and ethanol (1 g) were placed in a 10 mL aluminum aerosol vial. The vial was cooled to about −78° C. in a dry ice/trichloromethane bath then filled with cold P134a (1,1,1,2-tetrafluoroethane, 8.95 g). The resulting formulation contained 0.5% by weight of butixocort propionate, 10% by weight ethanol, and 89.5% by weight P134a. The vial was sealed with a 50 µL metered dose valve having a diaphragm of DB-218 nitrile rubber (American Gasket and Rubber, Schiller Park, Ill.). The respirable fraction was found to be 42% using the test method described above and an actuator having a generally elliptical orifice 0.422 mm (0.0166 in)×0.478 mm (0.0188 in). This formulation was tested for respirable fraction using an actuator having a generally elliptical orifice 0.22 mm (0.0086 in)×0.25 mm (0.0098 in) (Model M3756, 3M). Respirable fraction was found to be 69%.

EXAMPLE 2

Butixocort propionate (50 mg) and ethanol (1 g) were place in a 10 mL aluminum aerosol vial. The vial was sealed with a continuous valve then pressure filled with P227 (1,1,1,2,3,3,3-heptafluoropropane, 8.95 g). The resulting formulation contained 0.5% by weight of butixocort propionate, 10% by weight ethanol, and 89.5% by weight P227. The vial was chilled then the continuous valve was replaced with a 50 μL metered dose valve having a diaphragm of DB-218 nitrile rubber (American Gasket and Rubber, Schiller Park, Ill.). The respirable fraction was determined using the method described above and found to be 45%.

EXAMPLES 3-10

Solution formulations containing 10 percent by weight ethanol, 0.5 percent butixocort propionate, and either P 134a or P227 (as indicated in Table 3 below) were prepared and placed in aerosol vials of the several types shown in Table 3 below. The vials were sealed with blind ferrules. The vials were stored at 40° C. for one month then assayed according to the test method described above for percent degradation impurities and drug content. The results are shown in Table 3 below where each value is the average of 3 separate vials.

TABLE 3

| Example | Propellant | Vial Type | Drug Content (% of Initial Content) | Percent Impurities Initial | 1 Month |
|---|---|---|---|---|---|
| 3 | 134a | Glass[1] (Type III) | 79.7 | 1.53 | 6.39 |
| 4 | 134a | Aluminum[2] | 98.0 | 1.41 | 2.95 |

TABLE 3-continued

| Example | Propellant | Vial Type | Drug Content (% of Initial Content) | Percent Impurities Initial | 1 Month |
|---|---|---|---|---|---|
| 5 | 134a | Epoxy-Lined Aluminum[3] | 100 | 1.82 | 1.25 |
| 6 | 134a | Plastic[4] | 95.7 | 2.42 | 3.53 |
| 7 | 227 | Glass (Type III) | 87.5 | 1.48 | 6.67 |
| 8 | 227 | Aluminum | 81.5 | 1.46 | 3.80 |
| 9 | 227 | Epoxy-Lined Aluminum | 93.3 | 2.49 | 2.66 |
| 10 | 227 | Plastic | 93.2 | 2.27 | 5.13 |

[1]Made from Type-III (soda-lime) glass and are avaiable from Wheaton Coated Products
[2]Available from 3M Company
[3]Epoxy/phenol-formaldehyde resin coated aluminum vials, coated by Cebal
[4]Made from polyethylene terephthalate and are available from Precise Plastic Ltd., United Kingdom

EXAMPLES 11-50

Solution formulations as set forth in Table 4 were prepared, placed in aerosol vials having diaphragms and seals of nitrile rubber (DB-218, American Gasket and Rubber, Schiller Park, Ill.), stored at 40° C., and tested for percent drug recovery according to the method described above. Each entry represents the average of 3 independent determinations. The designation "% w/w" indicates percent by weight of the indicated component based on the total weight of the formulation. Vial types are those described in TABLE 3 above.

TABLE 4

| Example | Vial Type | Propellant (weight % P134a: weight % P227) | Ethanol % w/w | Water % w/w | Sorbitan trioleate % w/w (× 0.001) | Stability Results 10 Month % Recovery |
|---|---|---|---|---|---|---|
| 11 | Aluminum | 0:100 | 8 | 0.00 | 0.0 | 95.8 |
| 12 | Epoxy-lined | 0:100 | 8 | 0.00 | 5.0 | 63.9 |
| 13 | Aluminum | 100:0 | 8 | 0.00 | 5.0 | 91.8 |
| 14 | Epoxy-lined | 100:0 | 8 | 0.00 | 0.0 | 80.2 |
| 15 | Aluminum | 0:100 | 16 | 0.00 | 5.0 | 91.2 |
| 16 | Epoxy-lined | 0:100 | 16 | 0.00 | 0.0 | 86.7 |
| 17 | Aluminum | 100:0 | 16 | 0.00 | 0.0 | 89.7 |
| 18 | Epoxy-lined | 100:0 | 16 | 0.00 | 5.0 | 72.1 |
| 19 | Aluminum | 0:100 | 8 | 0.50 | 5.0 | 95.7 |
| 20 | Epoxy-lined | 0:100 | 8 | 0.50 | 0.0 | 90.5 |
| 21 | Aluminum | 100:0 | 9 | 0.50 | 0.0 | 94.3 |
| 22 | Epoxy-lined | 100:0 | 8 | 0.50 | 5.0 | 89.0 |
| 23 | Aluminum | 0:100 | 16 | 0.50 | 0.0 | 96.1 |
| 24 | Epoxy-lined | 0:100 | 16 | 0.50 | 5.0 | 92.2 |
| 25 | Aluminum | 100:0 | 16 | 0.50 | 5.0 | 96.1 |
| 26 | Epoxy-lined | 100:0 | 16 | 0.50 | 0.0 | 88.5 |
| 27 | Epoxy-lined | 50:50 | 12 | 0.25 | 2.5 | 82.2 |
| 28 | Epoxy-lined | 50:50 | 12 | 0.25 | 2.5 | 81.5 |
| 29 | Epoxy-lined | 50:50 | 12 | 0.25 | 2.5 | 87.5 |
| 30 | Epoxy-lined | 50:50 | 12 | 0.25 | 2.5 | 89.3 |
| 31 | Aluminum | 0:100 | 8 | 0.00 | 5.0 | 95.3 |
| 32 | Epoxy-lined | 0:100 | 8 | 0.00 | 0.0 | 88.3 |
| 33 | Aluminum | 100:0 | 8 | 0.00 | 0.0 | 97.3 |
| 34 | Epoxy-lined | 100:0 | 8 | 0.00 | 5.0 | 81.7 |
| 35 | Aluminum | 0:100 | 16 | 0.00 | 0.0 | 94.1 |
| 36 | Epoxy-lined | 0:100 | 16 | 0.00 | 5.0 | 82.6 |
| 37 | Aluminum | 100:0 | 16 | 0.00 | 5.0 | 69.7 |
| 38 | Epoxy-lined | 100:0 | 16 | 0.00 | 0.0 | 65.4 |
| 39 | Aluminum | 0:100 | 8 | 0.50 | 0.0 | 95.8 |
| 40 | Epoxy-lined | 0:100 | 8 | 0.50 | 5.0 | 90.3 |
| 41 | Aluminum | 100:0 | 8 | 0.50 | 5.0 | 93.8 |

TABLE 4-continued

| Example | Vial Type | Propellant (weight % P134a: weight % P227) | Ethanol % w/w | Water % w/w | Sorbitan trioleate % w/w (× 0.001) | Stability Results 10 Month % Recovery |
|---|---|---|---|---|---|---|
| 42 | Epoxy-lined | 100:0 | 8 | 0.50 | 0.0 | 86.4 |
| 43 | Aluminum | 0:100 | 16 | 0.50 | 5.0 | 97.3 |
| 44 | Epoxy-lined | 0:100 | 16 | 0.50 | 0.0 | 91.3 |
| 45 | Aluminum | 100:0 | 16 | 0.50 | 0.0 | 96.8 |
| 46 | Epoxy-lined | 100:0 | 16 | 0.50 | 5.0 | 87.6 |
| 47 | Epoxy-lined | 50:50 | 12 | 0.25 | 2.5 | 87.1 |
| 48 | Epoxy-lined | 50:50 | 12 | 0.25 | 2.5 | 88.0 |
| 49 | Epoxy-lined | 50:50 | 12 | 0.25 | 2.5 | 87.5 |
| 50 | Epoxy-lined | 50:50 | 12 | 0.25 | 2.5 | 87.5 |

What is claimed is:

1. A solution aerosol formulation comprising: a propellant system comprising a hydrofluorocarbon selected from the group consisting of 1,1,1,2-tetrafluoroethane, 1,1,1,2,3,3,3-heptafluoropropane, and a mixture thereof; and a therapeutically effective amount of butixocort propionate, wherein the butixocort propionate is dissolved in the formulation and is the sole drug in the formulation.

2. An aerosol formulation according to claim 1, wherein the propellant comprises 1,1,1,2-tetrafluoroethane.

3. An aerosol formulation according to claim 1, wherein the propellant comprises 1,1,1,2,3,3,3-heptafluoropropane.

4. An aerosol formulation according to claim 1, wherein the propellant comprises a mixture of 1,1,1,2-tetrafluoroethane and 1,1,1,2,3,3,3-heptafluoropropane.

5. An aerosol formulation according to claim 1, wherein the butixocort propionate is present in an amount of about 0.1 percent to about 0.9 percent by weight.

6. An aerosol formulation according to claim 1, characterized in that it is free of chlorofluorocarbons.

7. An aerosol formulation according to claim 1, further comprising ethanol.

8. An aerosol formulation according to claim 7, wherein the ethanol is present in an amount of about 3 percent to about 30 percent by weight.

9. An aerosol formulation according to claim 8, wherein the ethanol is present in an amount of about 8 percent to about 16 percent by weight.

10. An aerosol formulation according to claim 1 further comprising about 0.005 percent to about 1 percent by weight water.

11. An aerosol formulation according to claim 1 further comprising a flavoring agent.

12. An aerosol formulation according to claim 1 comprising from about 0.1 percent to about 0.9 by weight butixocort propionate, from about 8 to about 16 percent by weight ethanol, and 1,1,1,2,3,3,3-heptafluoropropane.

13. An aerosol formulation according to claim 1 comprising from about 0.1 percent to about 0.9 percent by weight butixocort propionate, from about 8 to about 16 percent by weight ethanol, and 1,1,1,2-tetrafluoroethane.

14. An aerosol formulation according to claim 1, wherein the formulation exhibits at least 93 percent drug recovery after storage for ten months at 40° C. in an aluminum aerosol canister.

15. A method of treating bronchial asthma comprising administering via inhalation an amount of a formulation according to claim 1 so as to control inflammation associated with bronchial asthma.

16. A metered dose inhaler comprising: (i) an aerosol canister defining a formulation chamber; and (ii) a formulation according to claim 1, wherein said formulation is contained within said formulation chamber.

* * * * *